United States Patent
Dorogi et al.

[11] Patent Number: 6,063,387
[45] Date of Patent: May 16, 2000

[54] ANHYDROUS COSMETIC COMPOSITION WITH CERAMIDES FOR FIRMING SKIN

[75] Inventors: Peter Ladislaus Dorogi, Norwalk; David Canestrari, Killngworth; Alan Joel Meyers, Trumbull; Anthony Vargas, Monroe, all of Conn.

[73] Assignee: Elizabeth Arden Co., Division of Conopco, Inc., New York, N.Y.

[21] Appl. No.: 08/978,407

[22] Filed: Nov. 25, 1997

Related U.S. Application Data

[60] Provisional application No. 60/042,006, Apr. 17, 1997.

[51] Int. Cl.[7] ................................................. A61K 7/48
[52] U.S. Cl. ..................... 424/401; 424/78.02; 514/844
[58] Field of Search ............................... 424/401, 78.02; 514/844

[56] References Cited

U.S. PATENT DOCUMENTS

| | | |
|---|---|---|
| 4,950,688 | 8/1990 | Bowser et al. . |
| 5,063,057 | 11/1991 | Spellman et al. . |
| 5,451,691 | 9/1995 | Crawford et al. . |
| 5,476,661 | 12/1995 | Pillai et al. . |
| 5,885,595 | 3/1999 | Corey et al. ............................ 424/401 |

FOREIGN PATENT DOCUMENTS

| | | |
|---|---|---|
| 0 720 847 | 1/1995 | European Pat. Off. . |
| 0 676 194 | 10/1995 | European Pat. Off. . |
| 95/29151 | 11/1995 | WIPO . |
| 96/16635 | 6/1996 | WIPO . |

OTHER PUBLICATIONS

Ceramides Brochure, "Human Skin–identical Ceramides" by Lambers et al., 1984, pp. 2–8.

*Primary Examiner*—Jyothsna Venkat
*Attorney, Agent, or Firm*—Milton L. Honig

[57] ABSTRACT

A method and cosmetic composition for improving skin firmness are provided through an anhydrous composition including a hydrophobic carrier which may be a silicone or hydrocarbon for delivering an effective amount of a ceramide formed of a sphingoid base linked through an amide to a 2-hydroxycarboxylic $C_2$–$C_{30}$ group.

8 Claims, No Drawings

ANHYDROUS COSMETIC COMPOSITION WITH CERAMIDES FOR FIRMING SKIN

This application claims the benefit of Provisional Application Ser. No. 60/042,006 filed on Apr. 17, 1997.

BACKGROUND OF THE INVENTION

1. Field of the Invention

The present invention concerns a new ceramide composition and a method for improving the firmness of skin.

2. The Related Art

Aging of skin is accompanied by a number of visible changes. The freshness of youth may change through the appearance of age spots;, sallowness, mottled pigmentation, dryness and alteration in firmness or elasticity. These phenomena appear to a different extent in any particular person. These changes can and probably do arise from different biological aging mechanisms. For this reason, no single chemical antidote is likely to simultaneously address all of the aging changes. The present invention concerns itself with the problem improving the firmness aspect of skin.

Cosmetic science within the last decade has seen the commercial advent of three broad categories of active skin agents. These are the cerarmides, alpha-hydroxycarboxylic acids (known as AHAS) and the retinoids. U.S. Pat. No. 4,950,688 (Bowser et al.) is one of the earliest references describing the synthesis and chemistry of ceramide 1 and its derivatives. WO 96/163635 (Lambers et al.) reports ceramide-containing compositions having a nigh capacity for recovering diminished water-retaining properties of pretreated or damaged skin. WO 95/29151 (Lambers et al.) describes synthesis procedures to obtain 2-alpha-hydroxycarboxylic acid based ceramide derivatives. EP 0 720 847 (Leveque et al.) describes use of ceramide 6 as a principle agent for reducing the loss of water from the skin and/or from keratin fibers. Cosmoferm, a division of Gist-brocades NV in a brochure (entitled "Human Skin-identical Ceramides", presented at an annual meeting of the British Society of Cosmetic Chemists, November 1994) provides an overview of ceramide chemistry. Related technology is disclosed in U.S. Pat. No. 476,661 (Pillai et al.) and U.S. Pat. No. 5,451,691 (Crawford et al.).

Ceramides have been delivered to the consumer in a variety of packages. The Elizabeth Arden Company was a pioneer in this area with a product known as "Ceramide Time Complex Capsules". Therein ceramide 1 and/or ceramide 3 were delivered in a cosmetic composition dispensed from a saturn-shaped gelatin capsule. See U.S. Pat. No. 5,063,057 (Spellman et al.).

Combinations of ceramide, alpha-hydroxycarboxylic acids and retinoids have been reported in EP 0 676 194 A2 (L'Oreal).

Despite the evident high level of activity, none of the aforementioned technology has addressed the issue of firming skin.

Accordingly, it is an object of the present invention to provide a cosmetic composition and method with the ability to achieve a perceptible improvement in the firmness of skin.

Another object of the present invention is to provide a cosmetic formula that not only improves firmness of skin but also lacks the irritation characteristics of previous systems incorporating ceramides, alpha-hydroxycarboxylic acids and/or retinoids.

These and other objects of the present invention will become more readily apparent from consideration of the following summary and detailed discussion.

SUMMARY OF THE INVENTION

An anhydrous cosmetic composition is provided which includes:
- (i) from 50 to 99.9% by weight of a hydrophobic carrier selected from the group consisting of silicones, hydrocarbons and mixtures thereof; and
- (ii) an effective amount to firm skin of a ceramide formed of a sphingoid base linked through an amide to a 2-hydroxycarboxylic $C_2$–$C_{30}$ group.

A method for improving the firmness of skin is also provided wherein an anhydrous cosmetic composition is applied to the skin, the composition including:
- (i) from 50 to 99.9% by weight of a hydrophobic carrier selected from the group consisting of silicones, hydrocarbons and mixtures thereof; and
- (ii) an effective amount to firm skin of a ceramide formed of sphingoid base linked through an amide to a 2-hydroxycarboxylic $C_2$–$C_{30}$ group. 26

DETAILED DESCRIPTION

Now it has been found that the incorporation of ceramides with a sphingoid base structure linked through an amide to a 2-hydroxycartioxylic $C_2$–$C_{30}$ group delivered in an anhydrous carrier provides a perceptible improvement in firming human skin.

Anhydrous systems of the present invention require a carrier in an amount from 50% to 99.9%, preferably from 75% to 99.5%, optimally from greater than 90% to 97% by weight. The carrier will be silicones and/or hydrocarbons.

Silicones may be divided into volatile and non-volatile varieties. The term "volatile" as used herein refers to those materials which have a measurable vapor pressure at ambient temperature. Volatile silicone oils are preferably chosen from cyclic or linear polydimethyl siloxanes containing from 3 to 9, preferably from 4 to 5 silicon atoms. Cyclic silicones are known as cyclomethicones. These are available commercially as Dow Corning Fluid 245 and Dow Corning 244.

Linear volatile silicone materials generally have viscosities less than about 5 centistokes at 25° C. while cyclic materials typically have viscosity of less than about 10 centistokes. The linear volatile silicones are commercially available as Dow Corning Fluid 344 and Dow Corning 345.

Nonvolatile silicones include polyalkyl siloxanes, polyalkylaryl siloxanes and polyether siloxane copolymers. The essentially non-volatile polyalkyl siloxanes useful herein include, for example, polydimethyl siloxanes with viscosities from 5 to 100,000 centistokes at 25° C. Among the preferred non-volatile silicones are those having viscosities from 10 to 400 centistokes at 25° C. These are known generally as dimethicones and are available as Dow Corning Fluid 200.

Particularly preferred for this invention is a combination of cyclomethicone and dimethicone in a ratio of 100:1 to 1:100, preferably from 50:1 to 1:10, optimally from 15:1 to 3:1 by weight of the carrier.

Hydrocarbons may be used either exclusively or in combination with silicones to serve as a carrier. These materials may be formed from $C_4$–$C_{50}$ hydrocarbons. Illustrative substances are petrolatum, isoparaffin, mineral oil, poly ($C_2$–$C_{10}$ alkenes) and combinations thereof. Preferred materials are isododecane and isohexadecane available from the Permethyl Corporation as Permethyl 99® and 101®. Other commercially available hydrocarbons are the polydecenes and polyoctenes available from the Ethyl Corporation.

Other representative hydrocarbons include squalane and squalene, which are naturally derived hydrocarbons formed from the biological conversion of isoprenes. These materials when present are preferably at levels from 1 to 20%, optimally from 2 to 10% by weight of the total composition.

A second critical component of the present invention is a type of ceramide characterized by a sphingoid base linked through an amide to a 2-hydroxycarboxylic $C_2$–$C_{30}$ group. Amounts may range from 0.00001 to 2%, preferably from 0.001 to 0.5%, more preferably 0.01 to 0.4%, optimally from 0.05 to 0.3% by weight. The sphingoid base may be either a sphingosine or a phytosphingosine. The amide linkage may be to the following 2-hydroxycarboxylic compounds:

2-hydroxyethanoic acid 2-hydroxypropanoic acid 2-methyl 2-hydroxypropanoic acid 2-hydroxybutanoic acid 2-hydroxypentanoic acid 2-hydroxyhexanoic acid 2-hydroxyheptanoic acid 2-hydroxyoctanoic acid 2-hydroxynonanoic acid 2-hydroxydecanoic acid 2-hydroxyundecanoic acid 2-hydroxydodecanoic acid 2-hydroxytetradecanoic acid 2-hydroxyhexadecanoic acid 2-hydroxyoctadecanoic acid 2-hydroxydocosanoic acid 2-hydroxydodocosanoic acid 2-hydroxytetradocosanoic acid 2-hydroxyhexadocosanoic acid 2-hydroxytriacontanoic acid Most preferred is the ceramide 6 class, especially ceramide 6a and 6b.

Another useful component of compositions of the present invention are the $C_{10}$–$C_{30}$, preferably $C_{18}$–$C_{24}$ fatty acids and their triglyceride esters. Illustrative are isostearic acid, stearic acid, and behenic acid. Among suitable triglyceride esters are the borage seed oils and evening primrose oils, both of which contain long chain $C_{18}$–$C_{24}$ omega fatty acids. Amounts of the fatty acids may range from 0.1 to 10%, preferably from 0.5 to 6%, optimally from 1 to 4% by weight of the total composition.

Cosmetic compositions of the present invention may also include small amounts of retinoids, most preferably retinyl linoleate. Retinoids may be present from 0.001 to 2%, preferably from 0.02 to 1 % by weight of the composition.

Vitamins may also be included such as tocopherol (which may serve also as an antioxidant), as well as perfumes and anti-microbials.

Also particularly useful for the present invention are small amounts of $C_{14}$–$C_{20}$ omega hydroxyacid lactones, such as hexadecanolide known also as Juniperic lactone. These materials may be present from 0.001 to 1, preferably from 0.01 to 0.5%, optimally from 0.05 to 0.1 % by weight of the total composition.

The following examples will more fully illustrate selected embodiments of this invention. All parts, percentages and proportions referred to herein and in the appended claims are by weight of the composition unless otherwise indicated.

EXAMPLE 1

A clinical study was conducted to evaluate a formulation outlined under Table I for its effect upon improving skin firmness.

TABLE I

| INGREDIENT | WEIGHT % |
|---|---|
| Cyclomethicone | 80.65 |
| Dimethicone | 9.60 |
| Squalane | 6.00 |
| Isostearic Acid | 1.90 |
| Borage (Borago Officinalis) Seed Oil | 0.90 |
| Retinyl Palmitate | 0.50 |
| Tocopherol | 0.25 |
| Ceramide 6 | 0.10 |
| Hexadecanolide | 0.05 |
| Retinyl Linoleate | 0.05 |
| Sphingolipids | 0.000040 |

Protocol of the Study The study was a double-blinded, controlled usage evaluation employing 50 subjects. Neither the subjects nor the investigator knew the identity of the test product. Duration of the study was 12 weeks.

Subjects participated in baseline examinations, bioinstrumentation and photography. Most especially, ballistometer measurements were taken on the left temple area of each subject. Prior to these measurements at each visit, the left temple area was marked using a plastic template fitting over the ear and reaching beyond the temple. One small dot was marked on the skin through a whole in the template over the temple area. Each subject received a baseline ballistometer measurement (an average of three readings) on the designated area on the left temple. Immediately after the baseline measurement was taken, a clinician applied the test product. At least five but not longer than Fifteen minutes after product application, subjects received a second ballistometer measurement (also an average of three readings) in the same area. Follow-up visits/measurements were conducted 4, 8 and 12 weeks subsequent to the initial visit.

For each visit, all clinical grading and ballistometer measurements were statistically compared to baseline. Results are reported in Table II.

TABLE II

| TIME POINT | MEAN CHANGE FROM BASELINE | MEAN % CHANGE |
|---|---|---|
| 5 minutes | −0.44 | — |
| 1 month | 0.98* | 6.6 |
| 2 months | 1.46* | 9.8 |
| 3 months | 0.31* | 3.3 |

*Statistically significant (p < 0.05) vs. Baseline

Based on the results in Table III covering the 3 month clinical, the ballistometer readings indicated a statistically significant increase in skin firmness.

EXAMPLES 2–10

A series of formulas falling within the present invention are outlined under Table III.

TABLE III

| INGREDIENT | 2 | 3 | 4 | 5 | 6 | 7 | 8 | 9 | 10 |
|---|---|---|---|---|---|---|---|---|---|
| Cyclomethicone | 80.00 | 85.00 | — | — | 4.00 | 90.00 | — | — | 90.00 |
| Isododecane | 7.00 | 2.00 | 80.00 | 80.00 | 70.00 | — | — | 10.00 | — |
| Isohexadecane | — | — | 10.00 | 10.00 | 20.50 | — | 85.00 | 85.00 | — |
| Polydecene | 5.00 | 5.00 | — | — | 5.00 | 5.00 | — | 3.00 | — |
| Squalene | 5.00 | 5.00 | 5.00 | 5.00 | — | 4.65 | 5.70 | — | 9.00 |
| Isostearic Acid | 2.20 | 2.20 | — | — | — | — | — | — | — |
| Behenic Acid | — | — | 4.60 | 4.40 | — | — | 8.00 | — | — |
| Ceramide 6a | 0.50 | — | 0.10 | 0.20 | — | 0.05 | — | — | — |
| Ceramide 6b | — | 0.50 | — | — | 0.20 | — | 1.00 | 0.80 | 0.20 |
| Tocopherol | 0.10 | 0.10 | 0.10 | — | 0.10 | 0.10 | 0.10 | 0.20 | 0.20 |
| Hexadecanolide | 0.10 | 0.10 | 0.10 | 0.20 | 0.10 | 0.10 | 0.10 | 0.50 | 0.20 |
| Retinyl Linoleate | 0.10 | 0.10 | 0.10 | 0.20 | 0.10 | 0.10 | 0.10 | 0.50 | 0.40 |

The foregoing description and examples illustrate selected embodiments of the present invention. In light thereof variations and modifications will be suggested to one skilled in the art, all of which are within the spirit arid purview of this invention.

What is claimed is:

1. An anhydrous cosmetic composition comprising:
   (i) from 50 to 99.9% by weight of a silicone, wherein the silicone is a combination of cyclomethicone and dimethicone in a weight ratio of 100:1 to 1:00; and
   (ii) an effective amount to firm skin of ceramide 6a or 6b, the composition being effective to improve the firmness of skin.

2. The product according to claim 1 further comprising from 0.1 to 10% by weight of a $C_{10}$–$C_{30}$ fatty acid or triglyceride ester thereof.

3. The composition according to claim 1 further comprising from 0.001 to 2% by weight of retinyl linoleate.

4. The composition according to claim 1 further comprising from 0.001 to 1% by weight of Juniperic lactone.

5. A method for improving the firmness of skin comprising applying to the skin an anhydrous cosmetic composition comprising:
   (i) from 50 to 99.9% by weight of a silicone; and
   (ii) an effective amount to firm skin of ceramide 6a and 6b.

6. The method according to claim 5 wherein the silicone is a combination of cyclomethicone and dimethicone in a weight ratio of 100:1 to 1:100 by weight of the carrier.

7. The method according to claim 6 further comprising from 0.001 to 1% by weight of retinyl linoleate.

8. The method according to claim 6 further comprising from 0.001 to 1% by weight of Juniperic lactone.

* * * * *